United States Patent [19]
Bauerfeind et al.

[11] Patent Number: 5,743,866
[45] Date of Patent: Apr. 28, 1998

[54] TUBULAR BANDAGE FOR PARTS OF THE HUMAN BODY

[75] Inventors: Hans B. Bauerfeind; Holger Reinhardt, both of Kempen, Germany

[73] Assignee: Bauerfeind GmbH & Co., Kempen, Germany

[21] Appl. No.: 750,200

[22] PCT Filed: May 31, 1995

[86] PCT No.: PCT/EP95/02064

§ 371 Date: Mar. 14, 1997

§ 102(e) Date: Mar. 14, 1997

[87] PCT Pub. No.: WO95/32693

PCT Pub. Date: Dec. 7, 1995

[30] Foreign Application Priority Data

Jun. 1, 1994 [DE] Germany .............. 44 19 260.6

[51] Int. Cl.[6] .................................................. A61F 5/00
[52] U.S. Cl. .................................... 602/63; 602/62
[58] Field of Search .......................... 602/5, 20, 23, 602/26, 60–63, 19

[56] References Cited

U.S. PATENT DOCUMENTS

| | | | |
|---|---|---|---|
| 3,406,406 | 10/1968 | Lutz | 602/62 X |
| 3,845,769 | 11/1974 | Shaw | 602/62 |
| 3,856,008 | 12/1974 | Fowler et al. | |
| 4,036,220 | 7/1977 | Bellasalma | |
| 4,130,115 | 12/1978 | Taylor | 602/16 |
| 4,176,665 | 12/1979 | Terpening | 602/62 X |
| 4,366,813 | 1/1983 | Nelson | 602/26 |
| 4,379,463 | 4/1983 | Meier et al. | 602/16 |
| 4,653,492 | 3/1987 | Parsons | |
| 5,507,722 | 4/1996 | Richardson | 602/63 X |
| 5,512,039 | 4/1996 | White | 602/63 X |
| 5,527,270 | 6/1996 | Chase et al. | 602/63 X |

FOREIGN PATENT DOCUMENTS

| | | |
|---|---|---|
| 34 41 496 C1 | 11/1984 | Germany . |
| 35 11 250 A1 | 3/1985 | Germany . |
| 90 17 540.9 | 12/1990 | Germany . |
| 92 11 728.7 | 8/1992 | Germany . |
| 42 30 165.3 | 9/1992 | Germany . |
| 44 19 260 C2 | 6/1994 | Germany . |

*Primary Examiner*—Linda C. Dvorak
*Attorney, Agent, or Firm*—Bardehle, Pagenberg, Dost, Altenburg, Frohwitter, Geissler

[57] ABSTRACT

A tubular bandage for parts of the human body, the bandage comprising: an elastic part, a significantly less elastic part, and straps which are of significantly less elastic longitudinal extensibility, or are nonelastic in the longitudinal direction, wherein the elastic part of the bandage comprises at least one insert incorporated with the significantly less elastic part to form a tubular configuration, wherein the straps are fixable to the significantly less elastic part across the elastic part such that when the straps are fixed the elasticity of the at least one insert is significantly reduced.

9 Claims, 2 Drawing Sheets

TUBULAR BANDAGE FOR PARTS OF THE HUMAN BODY

BACKGROUND OF THE INVENTION

The invention relates to a tubular bandage for parts of the human body, having elastic and less elastic parts. A bandage of this kind is described, for example, in DE-C 34 41 496. This patent relates to an ankle joint bandage in the form of a sock made of stretchable fabric, onto which a strip of nonstretchable material, e.g. of leather, has been sewn. The leather strip extends in this case from the upper end of the sock as far as the region of the sole of the foot. The leather strip serves to accommodate a thin bar of resilient material. A strap is laid obliquely over the leather strip :and is sewn to the sock, which strap forms one side of a hook-and-loop fastening for a wrap-around strap which consists of elastic and can be laid over the instep of the foot. The strap laid obliquely over the leather strip has no effect on the leather strip, but is used merely to fix the wrap-around strap.

It is additionally known to provide tubular bandages which consist entirely of elastic material with hook-and-loop fastening straps in order to have an effect on the positioning of the bandage (US-C 40 36 220, DE-U 92 11 728, DE-U 90 17 450). Moreover, the prior art includes elastic bandages which are composed of a strip of elastic material and are held together at the joining point or overlap point by hook-and-loop fastening straps (DE-A 42 30 165, US-C 38 56 008).

SUMMARY OF THE INVENTION

The invention is based on the object of making it easier to put on tubular bandages for parts of the human body without in the process losing the therapeutic action of the bandages. Taking a bandage having elastic and significantly less elastic parts as the starting point, the bandage according to the invention has incorporated in it at least one elastic part as a longitudinal strip extending over the entire length of the bandage, which, in addition to the longitudinal strip, comprises the significantly less elastic or nonelastic material, and the elastic parts are bridged by straps which are of significantly less elastic longitudinal extensibility, or are nonelastic in the longitudinal direction, such that, by fixing the straps on the bandage, the elasticity of the elastic parts is significantly reduced or eliminated.

Another bandage, which can be used to good effect primarily for the knee, contains two essentially identical elastic parts, one of which extends from one edge of the bandage to approximately the centre thereof and the other part of which extends from there to the other edge of the bandage, each part covering essentially half the circumference in the circumferential direction and the two parts being offset by 180° with respect to one another, and the elastic parts are bridged by straps which are of significantly less elastic longitudinal extensibility, or are nonelastic in the longitudinal direction, such that, by fixing the straps on the bandage, the elasticity of the elastic parts is significantly reduced or eliminated.

The elastic parts incorporated in the bandage firstly make it significantly easier to put on the bandage, since the elastic parts can stretch to such a degree that it is easily possible to pull the bandage over, for example, the ankle joint or the knee joint. After the bandage has been put on, its elasticity, which is undesirable for achieving a therapeutic action, is removed by fixing on the bandage the straps bridging the elastic parts, as a result of which any pulling on the elastic parts is completely absorbed by the straps bridging the latter.

The bandage thus loses its elasticity and, depending on the arrangement of the straps, becomes virtually nonelastic, so that, when the bandage is being worn, its virtual nonelasticity can act fully on the particular part of the body. Nonelasticity of this kind is desirable, for example, if limbs are to be immobilized or supported.

The bandage essentially containing two identical elastic parts can be expediently developed by incorporating in each case one rigid longitudinal bar with a hinge, the pin of which approximately coincides with the joint axis, in the bandage, in the region of the connections, running in the longitudinal direction of the bandage, of the elastic and of the less elastic parts. Such a bandage can easily be pulled over the knee joint and then fixed on the latter by the straps, the bars with the hinge ensuring that the knee joint can only bend in one direction, namely about the hinge pin.

Expediently, hook-and-loop fastenings are arranged on the straps for fixing the latter. The straps can in this case be pulled through reversing rings which are fastened on the bandage, by which means the straps can be tensioned comfortably.

BRIEF DESCRIPTION OF THE DRAWINGS

Exemplary embodiments of the invention are depicted in the figures, in which.

DETAILED DESCRIPTION OF THE INVENTION

Figure 1:
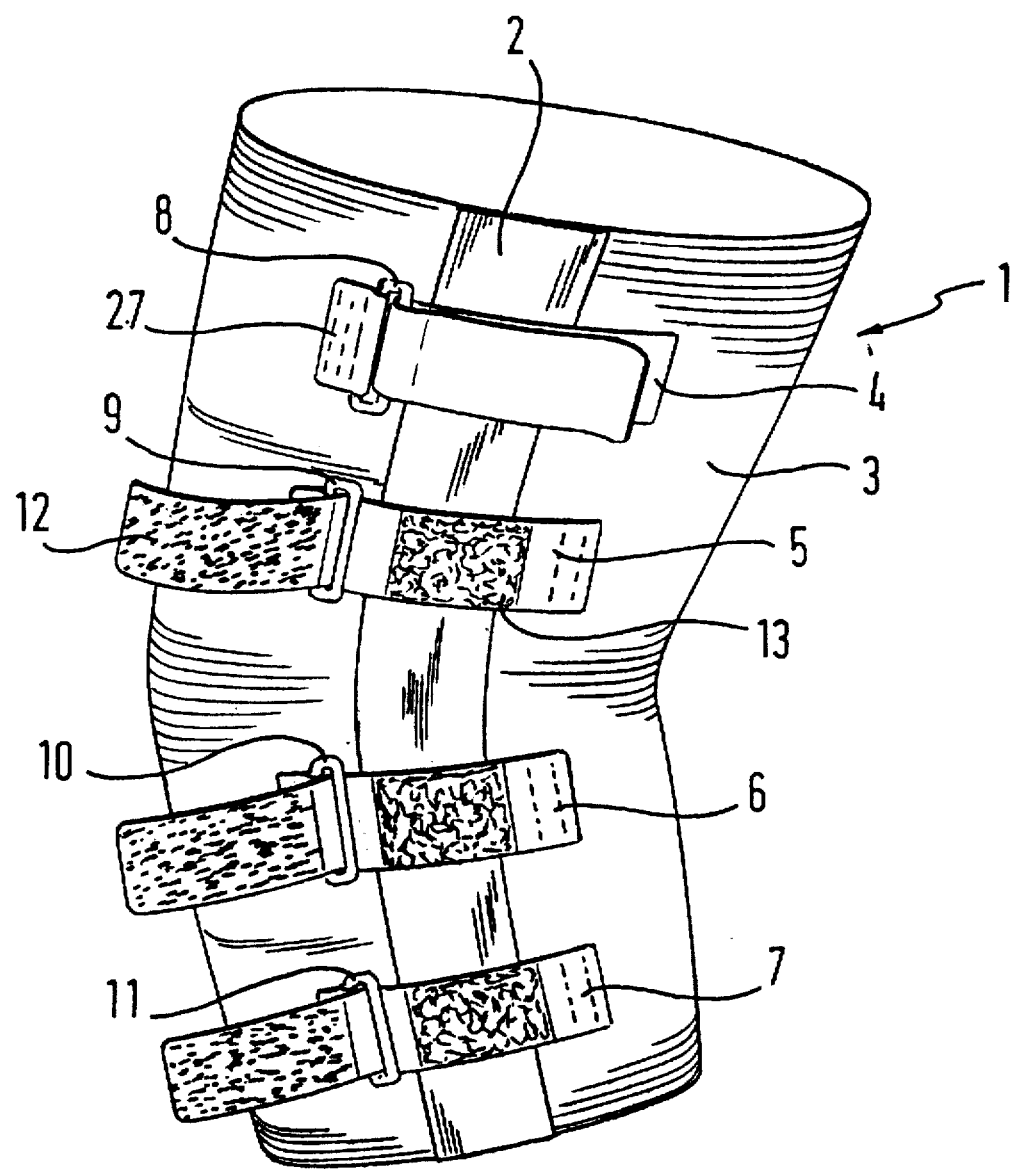
FIG. 1 shows a bandage with an essentially nonelastic longitudinal strip.

FIG. 1 shows the bandage 1 of tubular design, which, apart from the longitudinal strip 2, as its one part 3 is of essentially nonelastic design. This is because the part 3 consists of a nonstretchable fabric. The longitudinal strip 2, which consists of an elastic material, is incorporated, in particular woven or knitted, into the part 3. This longitudinal strip 2 makes it possible, when the bandage 1 is being pulled over a joint, e.g. the knee joint, for the bandage 1 to stretch in the region of the strip 2 and therefore to be able to be pulled over the joint in question effortlessly. The longitudinal strip 2, which thus forms the elastic part of the bandage 1, is bridged by the essentially nonelastic straps 4,5,6 and 7, which are fastened, in particular sewn, on their right-hand side in FIG. 1, on the nonelastic part 3. On the other side of the straps 4 to 7, the latter each have a ring 8,9,10 and 11, which for its part is fastened in a known manner on the nonelastic part 3 by means of a loop 27. Here, the loop is sewn onto the nonelastic part. In order to remove the effect of the elasticity from the elastic longitudinal strip 2, the straps 4–7 are pulled through the rings 8–11 and are pulled tight and fixed with respect to their active length by means in each case of a hook-and-loop fastening 12/13. The elastic longitudinal strip 2 is thus bridged by the nonelastic straps 4–7 and can no longer stretch.

Figure 2:
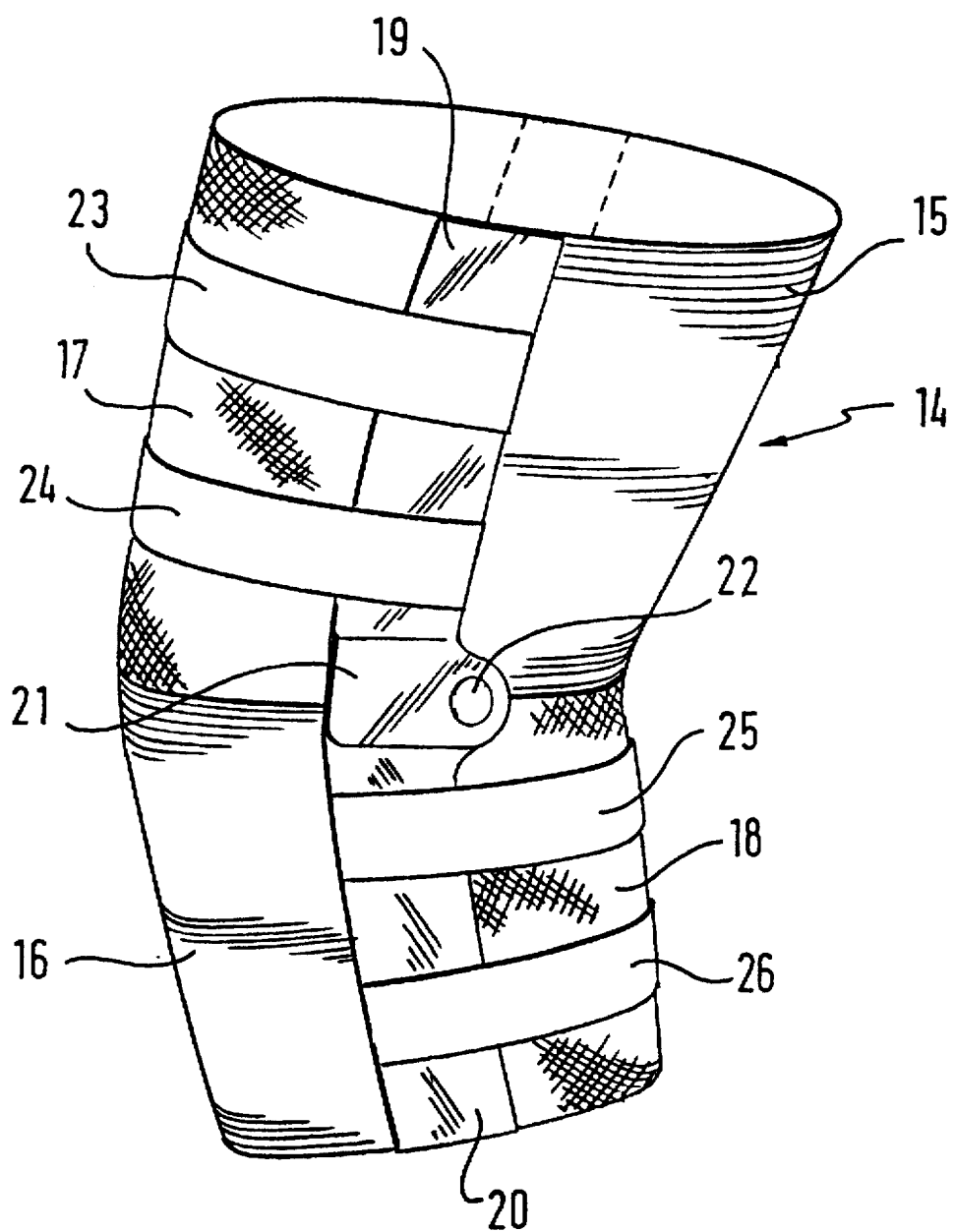
FIG. 2 shows a bandage with elastic parts offset with respect to one another.

FIG. 2 illustrates a variant in which the bandage 14 contains the two nonelastic parts 15 and 16 and the elastic parts 17 and 18. The nonelastic parts 15 and 16 are arranged diagonally to a certain extent, as are the elastic parts 17 and 18. In the region where the nonelastic parts 15/16 adjoin the elastic parts 17/18, longitudinal bars 19/20 are incorporated in the bandage 14, for example by means of an enclosing fabric which is sewn onto the material of the bandage 14. These longitudinal bars 19 and 20 in each case contain a hinge 21 with the pin 22, which lies approximately in the region of the joint axis and retains the mobility of the knee joint about the joint axis when the bandage 14 is put on over the knee joint. Longitudinal bars 19 and 20 of this kind are provided on both sides of the bandage 14 depicted in FIG. 2, but the rear longitudinal bar is not visible and is only indicated by dashed lines.

The elastic parts 17 and 18 of the bandage 14 are bridged by the nonelastic straps 23 and 24 and also 25 and 26, which bridge the associated elastic parts 17 and 18, respectively, in the same way as the straps 4–7 in accordance with FIG. 1 and thus remove the elasticity from these parts. The straps 23/24 and 25/26 are then fastened in the same way as is illustrated with reference to FIG. 1.

What is claimed is:

1. A tubular bandage for parts of the human body, said bandage comprising: an elastic part, a significantly less elastic part, and straps which are significantly less elastic in longitudinal extensibility, or are nonelastic in the longitudinal direction, wherein said elastic part of the bandage comprises at least one insert incorporated with said significantly less elastic part to form a tubular configuration, wherein said straps are fixable to said significantly less elastic part and extend across said elastic part such that when said straps are fixed the elasticity of said at least one insert is significantly reduced.

2. The bandage as claimed in claim 1, wherein the at least one insert is a longitudinal strip.

3. The bandage as claimed in claim 1, wherein said elastic part comprises first and second essentially identical elastic parts, wherein the first elastic part extends from a first end of the bandage to approximately the centre of the bandage and the second part extends from the center of the bandage to a second end of the bandage (14), wherein the first and second elastic parts each cover essentially half the circumference of the bandage in the circumferential direction, and wherein the first and second elastic parts are offset by 180° with respect to one another.

4. The bandage as claimed in claim 3 wherein the bandage is a bandage for joints, wherein the bandage further corn rises at least one rigid longitudinal bar with a hinge having a pin, wherein the pin approximately coincides with the joint axis, wherein the at least one rigid longitudinal bar is incorporated in the bandage in the in the longitudinal direction of the bandage in a region where the elastic part and the significantly less elastic parts are attached.

5. The bandage as claimed in claim 1, further comprising hook-and-loop fastenings arranged on the straps for fixing the straps.

6. The bandage as claimed in claim 5, further comprising reversing rings which are fastened on the bandage through which the straps are pullable.

7. The bandage as claimed in claim 2, further comprising hook-and-loop fastenings arranged on the straps for fixing the straps.

8. The bandage as claimed in claim 3, further comprising hook-and-loop fastenings arranged on the straps for fixing the straps.

9. The bandage as claimed in claim 4, further comprising hook-and-loop fastenings arranged on the straps for fixing the straps.

* * * * *